United States Patent [19]

Fischer

[11] Patent Number: 4,714,478

[45] Date of Patent: Dec. 22, 1987

[54] PROSTHESIS, METHOD, AND TOOL FOR INSTALLING SAME

[76] Inventor: William B. Fischer, 707 N. Fairbanks Ct., Chicago, Ill. 60611

[21] Appl. No.: 820,549

[22] Filed: Jan. 17, 1986

[51] Int. Cl.[4] ............................................. A61F 2/36
[52] U.S. Cl. ..................................................... 623/23
[58] Field of Search .................................... 623/16–23, 623/8

[56] References Cited

U.S. PATENT DOCUMENTS

| | | | |
|---|---|---|---|
| 3,064,645 | 11/1962 | Ficat et al. | 128/92 |
| 3,648,294 | 3/1972 | Shahrestani | 3/1.912 |
| 3,875,595 | 4/1975 | Froning | 623/17 |
| 4,032,994 | 7/1977 | Frey | 3/1.912 |
| 4,170,794 | 10/1979 | Zeibig et al. | 3/1.91 |
| 4,206,517 | 6/1980 | Pappas et al. | 3/1.91 |
| 4,318,191 | 3/1982 | Tepic | 3/1.913 |
| 4,562,598 | 1/1986 | Kranz | 623/20 |
| 4,592,755 | 6/1986 | Peutan et al. | 623/8 |

OTHER PUBLICATIONS

Roth, Alan I. et al., "A Surgical Technique for Decompression of the Femoral Head in Osteonecrosis", *Contemporary Orthopaedics*, vol. 11, No. 3, (Sep. 1985), pp. 13–17.

*Primary Examiner*—Richard J. Apley
*Assistant Examiner*—James Prizant
*Attorney, Agent, or Firm*—Willian Brinks Olds Hofer Gilson & Lione Ltd.

[57] ABSTRACT

An endoprosthesis which comprises a flexible, collapsible, hollow device which can be filled after it is positioned within the bone structure. In the case of a prosthesis designed to replace the ball of the femur, the endoprosthesis has a ball portion, a neck portion attached to and communicating with the ball portion, a body portion attached to and communicating with the neck portion, and an access opening opposite the ball portion. A method for installing the endoprosthesis in the hip is also described, in which a portal is drilled through the lateral cortex of the femur at a location opposite the ball, the ball of the femur is removed, and the endoprosthesis is inserted through the portal. Finally, the invention provides a special tool that can be used for removing the ball of the femur through a portal in the lateral cortex without dislocating the hip. Generally, this tool comprises a rotatable shaft, a blade received in an end portion of the shaft, and being hinged at its lower end, and means for extending and retracting the blade.

7 Claims, 11 Drawing Figures

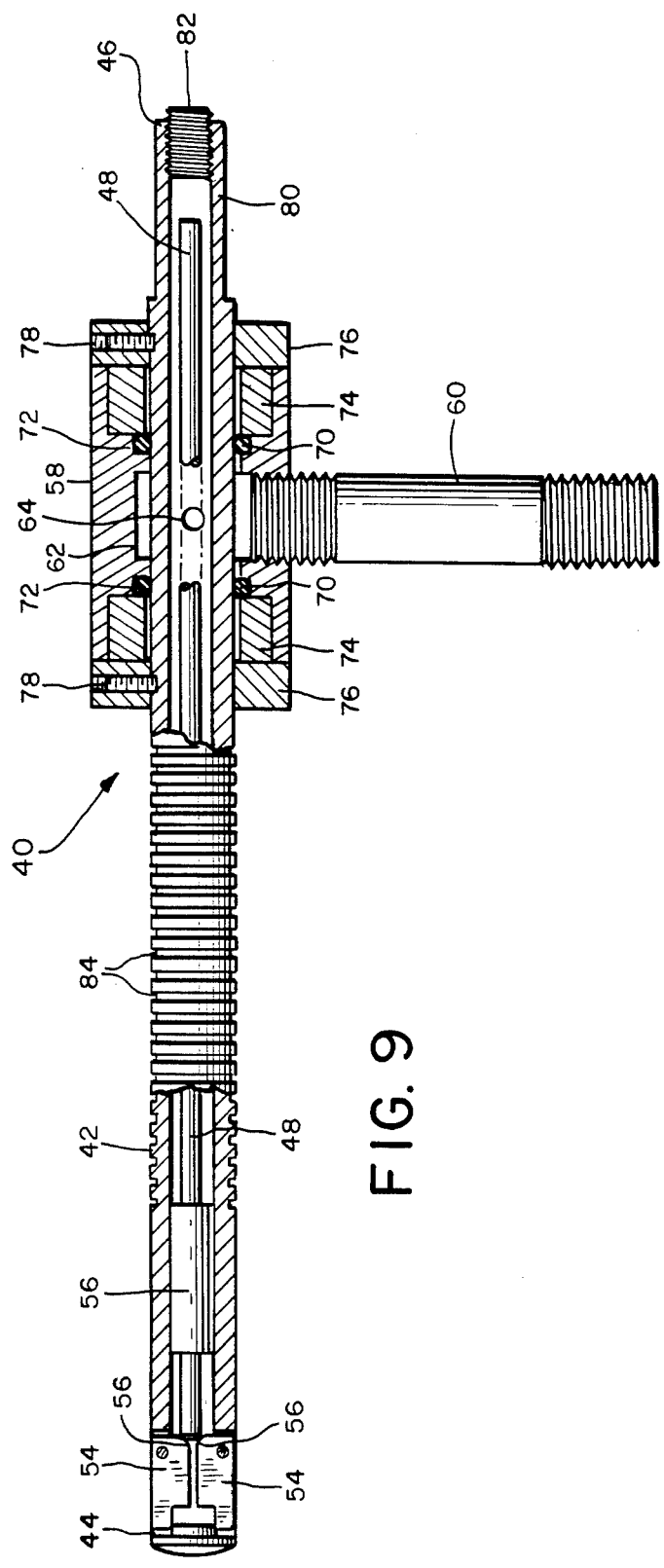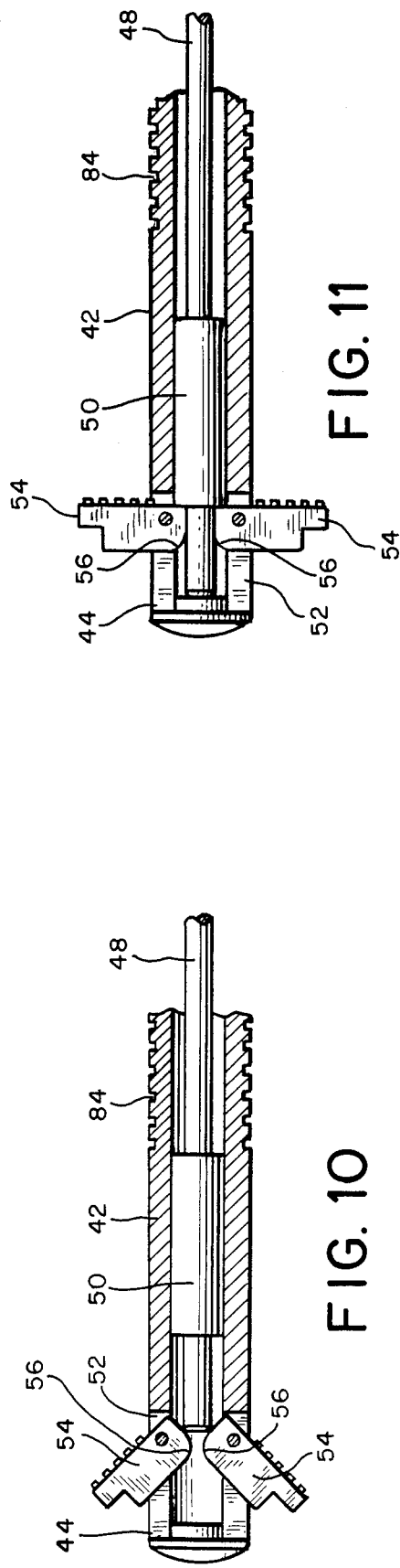

PROSTHESIS, METHOD, AND TOOL FOR INSTALLING SAME

BACKGROUND OF THE INVENTION

The present invention relates to an improved endoprosthesis, and more specifically to an improved endoprosthesis made of a hollow, collapsible plastic that can be filled after installation. The invention also relates to a method for installing such a prosthesis in a manner that makes possible a significant reduction in trauma to the patient.

In addition, the invention relates to a tool which enables the installation of a hip prosthesis embodying the present invention by removal of the ball of the femur through a portal in the lateral cortex.

As a result of injuries, arthritis and other diseases, as well as degenerative processes that result from aging and/or the use of certain drugs, it often becomes necessary to surgically replace a ball-and-socket joint, i.e., the shoulder or hip, with a prosthesis. In the hip, the replacement of the head, or ball, of the hip with a metal endoprosthesis has become a relatively common surgical procedure. Often the acetabular cup is also replaced in a procedure commonly referred to as a "total hip replacement."

Not only is such a procedure often required in humans, but it is also sometimes required in animals such as dogs. However, owing to the expense of such a procedure, it is rarely performed on animals.

The installation of a conventional endoprosthesis requires that extensive muscle tissue be cut in order to expose the joint structure. In the case of a hip endoprosthesis, the hip itself must then be dislocated, the ball and neck removed, and marrow removed from the bone. The endoprosthesis has a long stem portion which is then installed in the cavity left by the removed marrow. The endoprosthesis is then cemented into place with a suitable cement such as methyl methacrylate.

A significant problem with the use of metal endoprostheses is their tendency to work loose and to become separated from the bone structure. While there are several causes for this, such loosening is unquestionably promoted by the difference in hardness between the endoprosthesis and the much softer surrounding bone structure. Breaking loose is also promoted by the inability of a metal endoprosthesis to conform to the interior of the femur. That is, the endoprosthesis must be shaped so that it can be slid into the bone, and this shape inevitably promotes breaking loose. Finally, the fact that the endoprosthesis is made of metal prevents the normal bending and compression of the femur in the area proximal to the stem.

Another problem with conventional endoprostheses is the high expense involved. Not only do surgical procedures tend to be lengthy and expensive, but the endoprostheses themselves are a significant expense. Such devices are expensive to manufacture, and a variety of sizes must be carried in inventory, since it is important to obtain as close a fit as possible for the individual patient.

Loosening is a particular problem in the case of a hip endoprosthesis, since that area of the body is subjected to frequent motion and is required to carry weight. When loosening of the endoprosthesis occurs, the correction of this problem usually requires a second major surgical procedure to remove the endoprosthesis and substitute one with a larger stem in order to fill the now enlarged interior of the femur. Such surgical procedures can be extremely traumatic, particularly in older patients, among whom the majority of hip replacements are performed.

Previous efforts at overcoming these problems have primarily been directed at attempts to improve the bonding between the endoprosthesis and the surrounding bone structure. For example, it is widely believed that a major source of loosening is that the curing of commonly used cements is an exothermic reaction which itself destroys some of the tissue on the interior of the femur. Such tissue destruction reduces the ability of the patient's tissue to grow and form a bond with the endoprosthesis. In an effort to correct this problem, "cementless" metal endoprostheses have been developed, which rely on a roughened surface into which the tissue can grow. Because time is required for such tissue growth, cementless endoprostheses greatly extend the healing time following surgery. Moreover, because it is made of metal, a cementless endoprosthesis will still tend to transmit shock to the bone, and, in many cases, will still tend to work loose.

Another problem with conventional metal endoprostheses is that the hard metal ball tends to destroy the relatively soft tissue of the joint socket. Thus, when an endoprosthesis is installed alone, it often becomes necessary to later replace the socket. As is well known in the art, the replacement of the socket itself can lead to an additional set of difficulties in that the replacement socket may tend to come loose.

Owing to the trauma involved in the surgery, and to the aging of the population, there is a growing number of people who need joint replacements, especially hip replacements, but cannot tolerate such surgery. Thus, there is a need for an endoprosthesis that can be installed with a method that involves significantly reduced trauma to the patient.

SUMMARY OF THE INVENTION

The present invention alleviates or even overcomes these problems by providing an endoprosthesis which is less prone to becoming detached after installation, which has a reduced tendency to cause wear to the hip socket, and which can be installed using a simpler and less traumatic procedure than was required by prior-art devices.

Generally, the improved endoprosthesis of the present invention comprises a unitary flexible, collapsible, hollow device which can be filled after it is positioned within the bone structure. In the case of a prosthesis designed to replace the ball of the femur, the endoprosthesis has a ball portion, a neck portion attached to and communicating with the ball portion, a body portion attached to and communicating with the neck portion, and an access opening opposite the ball portion. Because of this hollow, collapsible design, the body portion can be shaped to conform to the interior of the intermedullary space, including the trochanteric region and the stem region. This conformance allows the endoprosthesis to be retained in place by the bone structure itself, without any need for cement.

In addition, it is contemplated that the endoprosthesis can be installed and replaced with procedures that are less invasive, and thus less traumatic to the patient. In accordance with the method of the present invention, a flexible, collapsible, hollow hip endoprosthesis is installed by drilling a portal through the lateral cortex of the femur at a location opposite the ball, removing the ball of the femur, and inserting the endoprosthesis through the portal. The endoprosthesis is then positioned within the femur and is filled with a suitable material.

The present invention also provides a special tool that can be used for removing the ball of the femur through a portal in the lateral cortex without dislocating the hip. Generally, this tool comprises a rotatable shaft, a blade received in an end portion of the shaft, and being hinged at its lower end, and means for extending and retracting the blade.

BRIEF DESCRIPTION OF THE DRAWINGS

FIG. 9 is a side elevation view, partially in cross section, of a tool according to the invention;

FIG. 10 is a fragmentary cross-sectional view showing the end portion of the tool shown in FIG. 9 with the cutting blades partially extended; and FIG. 11 is a fragmentary cross-sectional view similar to FIG. 10, showing the cutting blades fully extended.

DETAILED DESCRIPTION

Figure 1:
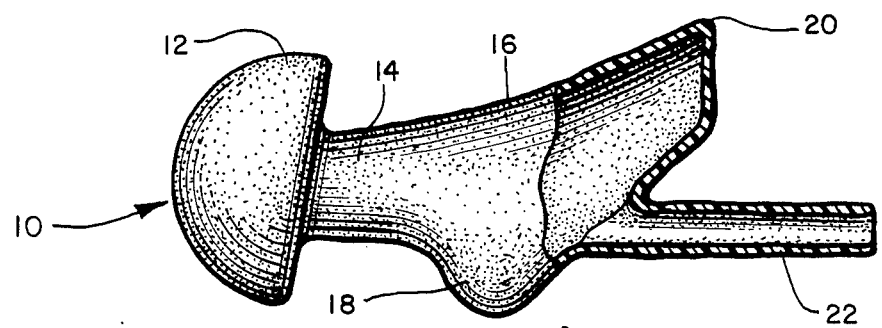
FIG. 1 is a side view of a hip endoprosthesis embodying the present invention, which is partially cut away to show the hollow interior thereof.
Figure 2:
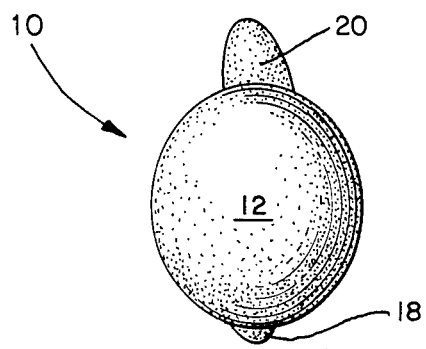
FIG. 2 is a top view thereof.
Figure 3:
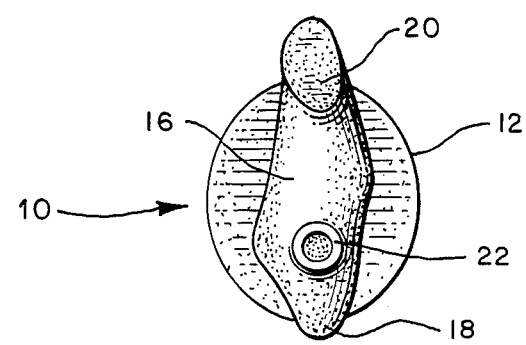
FIG. 3 is a bottom view thereof.

Referring to FIGS. 1-3, an endoprosthesis embodying the present invention is generally indicated by reference numeral 10. The endoprosthesis 10 is designed for use in the human hip. The endoprosthesis 10 is made of a flexible plastic material, and has a ball portion 12, a neck portion 14, and a body portion 16. The body portion 16 includes a trochanteric portion 18 and a stem portion 20. A hollow tube 22 projects from the bottom of the body portion 16 at a point opposite the ball portion 12. The tube 22 communicates with the interior of the endoprosthesis, as shown in FIG. 1.

Preferably, the endoprosthesis 10 will have a rough outer surface in order to help immobilize it within the femur, and to facilitate the engagement of the endoprosthesis with the surrounding tissue structure.

The endoprosthesis 10 can be installed using methods which are largely conventional, and which will be apparent to those skilled in the art. For example, a conventional "sunny side" incision can be made through the muscle, the hip dislocated, and the ball removed with a surgical saw. Because such a procedure involves considerable trauma to the patient, the technique described herein is preferred.

Figure 4:
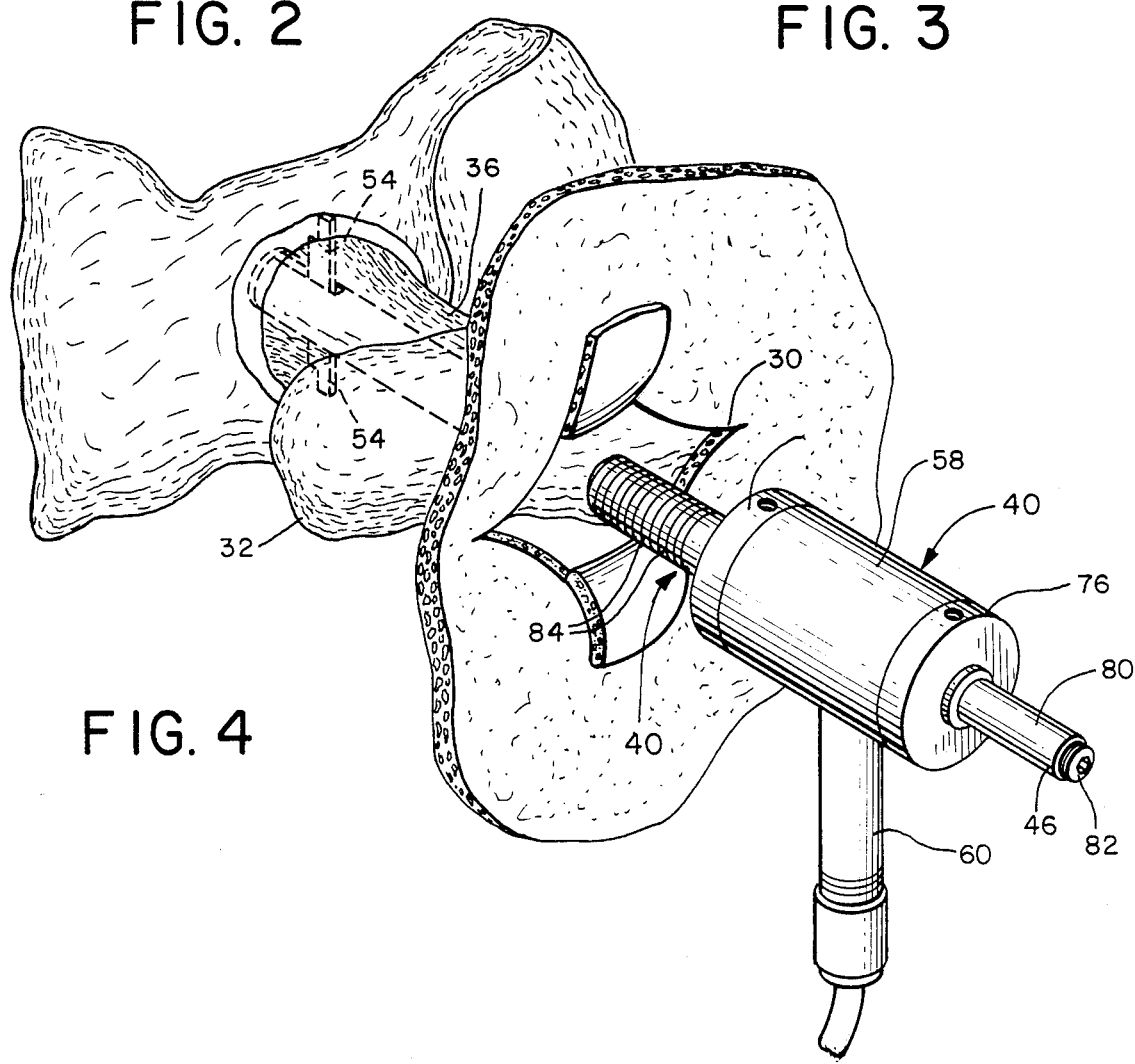
FIG. 4 is a fragmentary perspective view of a human hip, illustrating the manner in which the ball of the hip is removed.
Figure 5:
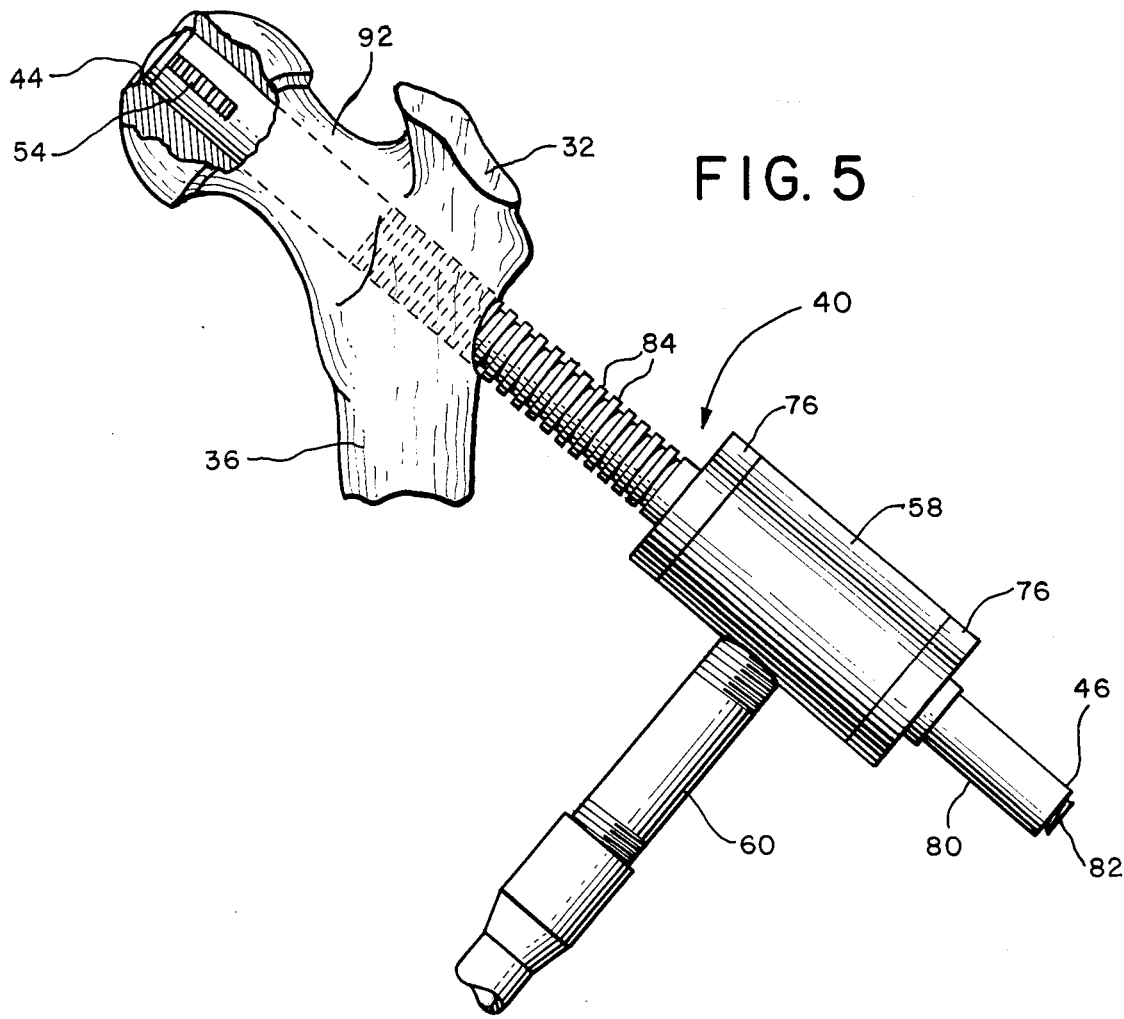
FIG. 5 is a perspective view of the upper portion of the femur, in which the view of the ball is partially cut away, showing the initial insertion of tool embodying the present invention.
Figure 6:
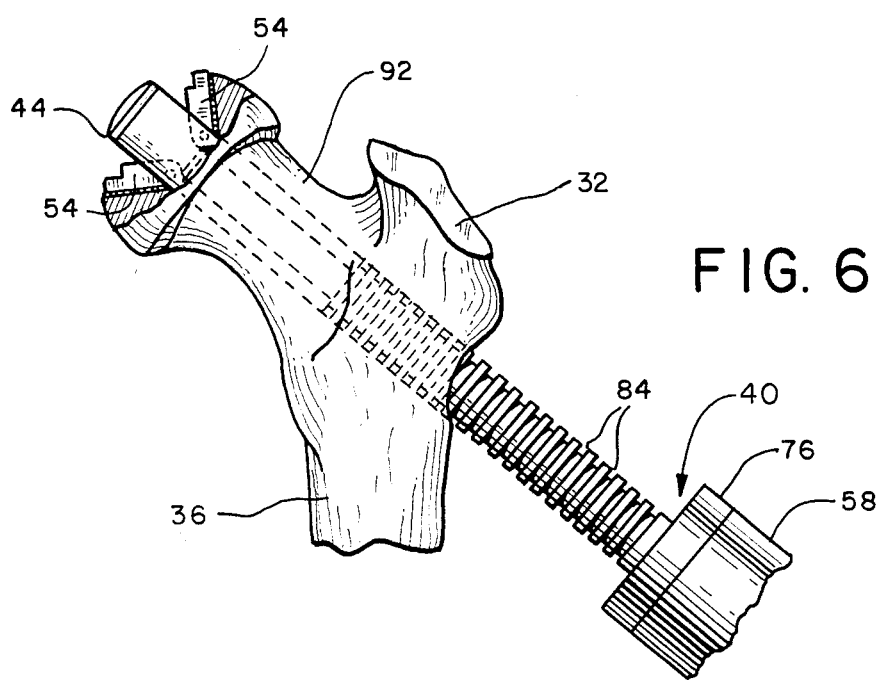
FIG. 6 is a perspective view similar to FIG. 5, showing the partial extension of the cutting blades of the tool during the cutting operation.

FIGS. 4-8 illustrate a preferred surgical procedure that may be used to install the endoprosthesis 10 with minimum trauma to the patient. Referring to FIGS. 4-6, in accordance with this method, the endoprosthesis 10 is installed by first making an incision 30 in the skin and tensor fascia adjacent the greater trochanter 32 and opposite the ball (not shown) of the femur 36. A pilot hole is then drilled with a guide pin (not shown) through the lateral cortex and the guide pin is passed through the center of the femoral neck. A larger portal is then drilled through the lateral cortex, centered on the pilot hole. Next, suitable x-ray equipment, such as a C-arm, is used to ensure proper centering of the guide pin in the head. A portal which is preferably about 0.5-1 inch in diameter is then drilled through the cortex. This portal should be as wide as the medullary space of the neck and should pass through the head of the ball. Up to this point, the procedure is well within the ability of those skilled in the art, and is similar to that used for compression head nailing for a fracture.

The next step in the installation procedure is the removal of the ball. As previously stated, this step may be accomplished by conventional techniques. However, while the neck is also conventionally removed, when using the endoprosthesis of the present invention, as much as possible of the neck should be preserved. In accordance with the preferred installation procedure, the novel tool of the present invention, generally indicated by reference numeral 40, is employed.

The detail of the tool 40 is best seen in FIGS. 9-11. The tool 40 includes a hollow, rotatable shaft 42 having a first end 44 and a second end 46. An inner drive pin 48 moves longitudinally within the shaft 42. The drive pin 48 incorporates a piston 50 which fits closely within the shaft 42 in order to provide for hydraulic actuation of the pin 48 while permitting the passage of liquid for irrigation as hereinafter described.

The first end 44 of the shaft 42 has slots 52 within which serrated cutting blades 54 are hingedly mounted. Although the tool 40 would perform its desired function with only one such blade, it is preferred to employ two oppositely disposed blades 54 as shown.

Each blade 54 has a cammed surface 56 which contacts the end of the drive pin 48 when the pin 48 is in the retracted position as shown in FIG. 9. It is thus seen that the piston 50 and drive pin 48 form means for extending and retracting the blades. As shown in FIG. 11, the cammed surface 56 is preferably designed to permit the end of the drive pin 48 to move past the blades 54, and to lock them in their fully extended position.

Referring to FIG. 9, the shaft 42 is free to rotate within a housing 58 having a liquid inlet conduit 60 on the side thereof. The liquid inlet conduit 60 communicates with a chamber 62 within the housing 58. The chamber 62 in turn communicates with the interior of the shaft 42 via an aperture 64. The housing 58 has a pair of O-rings 70 mounted in recesses 72 adjacent each side of the chamber 62 to prevent liquid from escaping from the chamber 62. The O-rings 70 are held in place by retainer rings 74, which, in turn, are held in place by end caps 76. The end caps 76 rotate with the shaft 42, and are held in place by set screws 78. The second end 46 of the shaft 42 has a narrowed portion 80, and is closed by a plug 82.

In the preferred embodiment, the piston 50 will not form a seal with the interior of the shaft 42. Thus, in operation, liquid under pressure will pass the piston and exit through the slots 52, irrigating the joint area during removal of the ball.

In the preferred embodiment shown, the shaft 42 has circumferential grooves 84 cut into it at regular intervals. These grooves 84 aid in measuring the penetration distance when using x-ray equipment.

Referring again to FIGS. 4–6, to remove the ball of the femur with the tool 40, the liquid inlet conduit is connected to a source of liquid under pressure. A sterile and biologically safe liquid, such as sterile Ringer's solution or saline solution, preferably with an antibiotic additive, should be employed. The narrowed portion 80 is connected to drive means, preferably driven through a flexible drive shaft (not shown). As best shown in FIG. 5, the first end 44 of the shaft 42 is then inserted into the previously drilled hole until the first end 44 passes through the ball and contacts the hip socket (not shown).

Fluid under pressure is delivered through the inlet conduit 60, exerting pressure against the piston 50 and urging the drive pin 48 toward the first end 44 of the shaft 42. The shaft is then rotated at a controlled rate of speed, preferably in the range of 0 to about 300 rpm. The slower rates are used at the beginning and end of the ball-removal procedure, while higher rates of speed can be used for removal of the major portion of the ball. As shown in FIGS. 6 and 10, the liquid pressure will cause the end of the pin 48 to push against the cammed surfaces 56 of the blades 54, urging them outwardly, while irrigating liquid passes through the slots 52.

As more of the ball is removed on each successive rotation, the blades will move farther outwardly until they reach the position shown in FIGS. 4 and 11. In that position, the cammed surfaces 56 have moved over center, permitting the pin 48 to move past them and to lock the blades 54 in their fully extended position, as previously described. Rotation of the shaft 42 is continued, while the shaft is slowly withdrawn, cutting away the remainder of the ball. The completion of this procedure is shown in FIG. 4.

After the ball has been entirely removed, the liquid pressure is stopped, and suction is applied, causing the pin 48 to move out of engagement with the blades 54. As the shaft 42 is withdrawn, the blades 54 will retract into the slots 52. The fragments left behind are then removed from the hip socket area by irrigation and aspiration.

Figure 7:
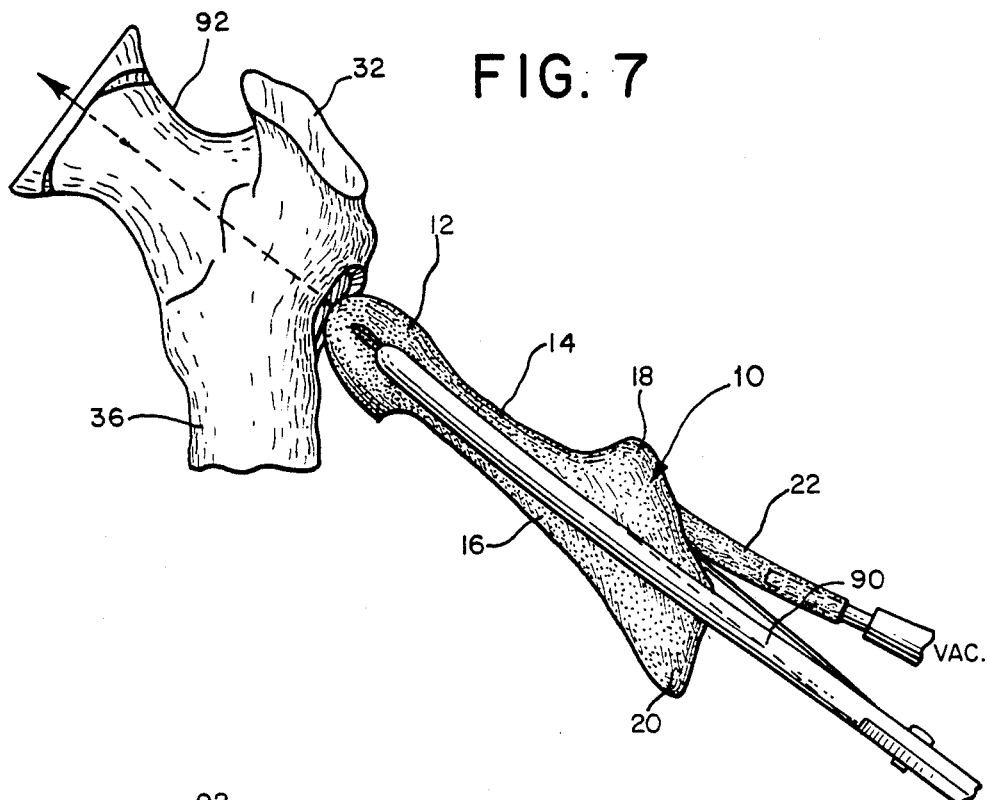
FIG. 7 is a perspective view similar to FIG. 5, showing the use of forceps to insert the collapsed endoprosthesis into the femur.

Referring now to FIG. 7, the next step is the insertion of the endoprosthesis 10. A suitable amount of marrow is removed from the interior of the femur 36 to allow room for the endoprosthesis 10. In the preferred installation method, the air is withdrawn from the endoprosthesis 10, and with the hollow tube 22 is closed off. The endoprosthesis 10 will therefore be collapsed, as shown in FIG. 7. The endoprosthesis 10 is then inserted through the portal in the femur using a forceps 90. As shown in FIG. 7, the endoprosthesis 10 is preferably folded to make it easier to insert it into the lateral portal. The endoprosthesis 10 should be passed through the femur 36 until the ball portion 12 seats on the femoral neck 92.

The next step is to fill the endoprosthesis 10. In accordance with the present invention, the endoprosthesis 10 can be filled with any suitable material, which can include liquids or particulate solids. Because of the possibility of eventual rupture of the wall of the endoprosthesis, any such material must, of course, be sterile and biologically safe.

Figure 8:
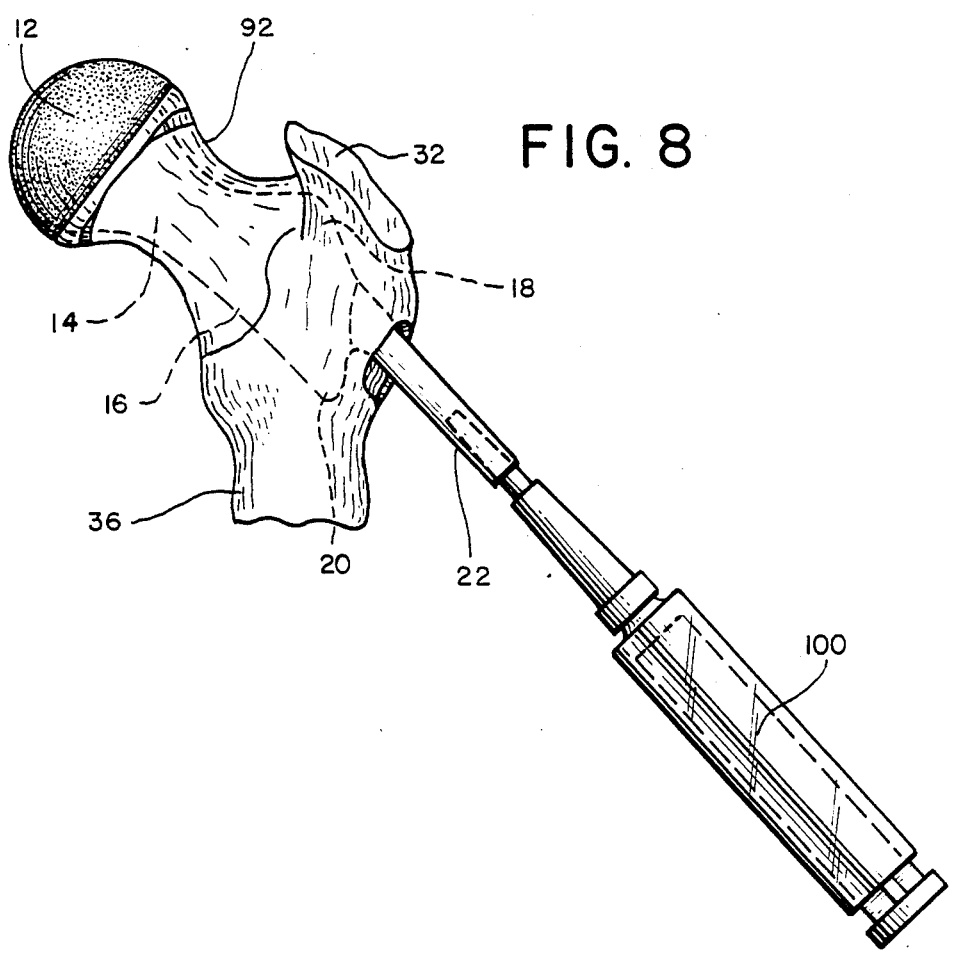
FIG. 8 is a perspective view similar to FIG. 5, showing the femur showing the inflation and filling of the endoprosthesis.

In accordance with the preferred embodiment, the endoprosthesis 10 is filled with a suitable plastic and curing agent. As shown in FIG. 8, this is preferably accomplished by mixing the two liquid components of the elastomer and placing them in a syringe 100 just prior to use. If the endoprosthesis 10 has already been evacuated, then the mixed elastomer components will simultaneously fill and inflate it. Once the elastomer is in place, the hollow tube 22 is cut off, and the incision is closed.

While the particular materials used to manufacture and fill the endoprosthesis 10 form no part of this invention, it is obvious that these materials must have certain characteristics. The plastic material used to form the endoprosthesis 10 must be resilient so that it will spring back to its original shape, and must be sufficiently flexible to permit the endoprosthesis 10 to be positioned within the femur as described above. The material must also have sufficient strength that it will not erode upon constant contact with the hip socket, and must also be compatible with body tissue. Finally, the material must be one that can be readily molded into the desired shape.

The presently preferred material for forming the endoprosthesis 10 is a silicone elastomer. Such materials are available as two separate components (elastomer and catalyst) from Dow Corning Corporation, Midland, Mich., under the trademark Silastic. Particularly preferred materials are marketed by Dow as Silastic Q7-4840 A/B Medical Grade Liquid Silicone Rubber and Silastic 382 Medical Grade Elastomer. These and other suitable elastomers are described and claimed in U.S. Pat. Nos. 3,445,420 and 4,162,243. These materials are also suitable for filling the endoprosthesis following insertion as previously described.

The endoprosthesis itself is preferably formed by molding, with the interior cavity being defined by a wax, which is subsequently removed by melting. Preferably, the wax has a melting point in the range of 200°–210° F. It is also important that the mold be evacuated prior to filling in order to minimize the formation of air bubbles. Such techniques are well within the skill of those familiar with the molding art.

Although the preferred embodiment of the endoprosthesis 10 described above is designed to replace the ball of the human hip, modifications of the device to render it suitable as a shoulder ball replacement will be obvious to those skilled in the art. Similarly, it will be obvious that an endoprosthesis embodying the present invention can be used in connection with the repair of ball-and-socket joints in animals such as dogs.

As those skilled in the art will also appreciate, although the presently preferred embodiment of the installation procedure involves the use of the particular tool described, other devices could be employed to remove the femoral ball through the lateral portal. Such devices not only include bladed tools of modified designs, but may also include cutting lasers and the like.

Obviously many modifications and variations of the invention as set forth herein will occur to those skilled in the art, and it is intended that the following claims will cover all such modifications and variations as fall within the true spirit and scope of the invention.

I claim:

1. A unitary, flexible, collapsible, hollow hip endoprosthesis comprising:
   a. a ball portion;

b. a neck portion attached to and communicating with the ball portion;

c. a body portion attached to and communicating with the neck portion, said body portion being shaped to conform to the interior of the intermedullary space, including the trochanteric region and the stem region; and d. an access opening in said body portion opposite the ball portion.

2. The endoprosthesis as defined in claim 1 further comprising a tubular portion extending outwardly opposite said ball portion and communicating with said access opening.

3. The endoprosthesis as defined in claim 2 wherein said endoprosthesis is formed of a silicone elastomer.

4. A method for installing a unitary, flexible, collapsible, hollow hip endoprosthesis comprising:
a. drilling a portal through the lateral cortex of the femur at a location opposite the ball;
b. removing the ball of the femur;
c. inserting said endoprosthesis through said portal;
d. positioning said endoprosthesis within the femur; and
e. filling said endoprosthesis.

5. The method as defined in claim 4 wherein said endoprosthesis is filled with a liquid plastic and curing agent.

6. The method as defined in claim 4 wherein said plastic is a silicone elastomer.

7. The method as defined in claim 4 wherein said endoprosthesis is installed without dislocating the hip.

* * * * *